United States Patent [19]
Vaartstra et al.

[11] Patent Number: 6,020,511
[45] Date of Patent: Feb. 1, 2000

[54] METHODS, COMPLEXES, AND SYSTEMS FOR FORMING METAL-CONTAINING FILMS

[75] Inventors: Brian A. Vaartstra, Nampa; Brenda D. Wanner, Meridian, both of Id.

[73] Assignee: Micron Technology, Inc., Boise, Id.

[21] Appl. No.: 09/140,134

[22] Filed: Aug. 25, 1998

Related U.S. Application Data

[60] Division of application No. 08/915,888, Aug. 21, 1997, Pat. No. 5,874,131, which is a continuation-in-part of application No. 08/725,033, Oct. 2, 1996, abandoned.

[51] Int. Cl.[7] .................................. C07F 5/06; C07F 5/02
[52] U.S. Cl. ................................ 556/176; 556/1; 534/15; 568/1; 568/3
[58] Field of Search ......................... 556/1, 176; 534/15; 568/1, 3

[56] References Cited

U.S. PATENT DOCUMENTS

| | | | |
|---|---|---|---|
| 5,151,305 | 9/1992 | Matsumoto et al. | 427/252 |
| 5,492,725 | 2/1996 | Gordon | 427/248.1 |
| 5,552,181 | 9/1996 | Kondoh et al. | 427/248.1 |

FOREIGN PATENT DOCUMENTS 295 876  11/1991  Germany .

OTHER PUBLICATIONS

Brown et al., "Diazabutadiene (DAB) Complexes of Aluminum. A New Mode of Coordination for a DAB Ligand", *Inorganic Chem.*, 34, 6415–6416 (1995).

Brown et al., "Gallium–Containing 6π–Electron Ring Systems", *J. Am. Chem. Soc.*, 117, 5421–5422 (1995).

Cloke et al., "Electronic Structure and Photoelectron Spectroscopy of $Al(Me_3CNCHCHNCMe_3)_2$ and $Ga(Me_3CNCHCHNCMe_3)_2$", *J. Chem. Soc., Dolton Transactions*, 2, 181–184 (1991).

Cloke et al., "Homoleptic Diazadiene Complexes of Titanium, Yttrium, and Some Lanthanoid Elements", *J. Chem. Soc., Chem. Commun.*, pp. 1344–1345 (1986).

Cloke et al., "Paramagnetic Aluminium–1,4–Di–t–butyl–1,4–diazabutadiene (dbdab) Complexes Derived from Metal Vapours and/or Metal Hydrides: Crystal Structures of $[Al(dbdab)_2]$ and $[Al(dbdab)\{(Bu^t)CH_2\{_2\}]$", *J. Chem. Soc., Chem. Comm.*, No. 20, 1394–1396, (1990).

Cloke et al., "Synthesis and X–Ray Crystal Structure of the First Homoleptic Main Group Diazadiene Complex, Bis(1,4–di–t–butyl–1,4–diazabuta–1,3–diene)gallium", *J. Chem. Soc., Chem. Commun.*, No. 15, 1002–1003 (1989).

Gluz et al., "Five– and Six– Membered Nonclassical 4π–Electron Heterocyclic Compounds Containing Boron and Aluminum: Quantum Chemical Study", *Russian J. Org. Chem.*, 31(3), 426–430 (1995).

Hara et al., "Stress in Al–Sc Interconnection Layers", *Jpn. J. Appl. Phys.*, 32, 1394–1396 (1993).

Henderson, "Reactions of Gallium Hydrides with 1,4–Di–t–butyl–1,4–diazabutadiene: Subvalent and Hydrometallation Products", *J. Chem. Soc., Chem. Commun.*, No. 17, 1203–1204 (1990).

Kaim et al., "Bis(1,4–di–tert–butyl–1,4–diazabutadiene)gallium is not a Gallium(∥) Compound", *J. Chem. Soc., Chem. Commun.*, No. 8, 597–598 (1991).

N. Kaltsoyannis, "Covalency in metal complexes of 1,4–diazabutadiene (dab). A density functional investigation of the electronic structures of $[M(dab)_2]$ (M=Li, Ga or Co) and $[Th(NH_3)(NH_2)_3(dab)]$", *J. Chem. Soc., Dalton Transactions*, 8, 1583–1589 (1996).

H. Kobayashi et al., "Electronic transfer between ligands in the tris(2,2'–bipyridine) complexes consisting of monoanion radicals", *Molecular Physics*, 78, 909–928 (1993).

P. Scott et al., "Synthesis, Structure and Electrochemistry of a Paramagnetic (1,4–Diazabutadiene) Thorium Complex", *J. Chem. Soc., Chem. Commun.*, No. 5, 579–580(1995).

S. Takayama "Effects of Y or Gd addition on the structures and resistivities of Al thin films", *J. Vac. Sci. Technol.*, 14, 2499–2504 (1996).

V. Versteeg, "Metalorganic Chemical Vapor Deposition by Pulsed Liquid Injection Using an Ultrasonic Nozzle: Titanium Dioxide on Sapphire from Titanium (IV) Isopropoxide", *J. Amer. Cer. Soc.*, 78, 2763–2768 (1995).

Atwood et al., Inorganic Chemistry, vol. 30, No. 25, pp. 4868–4870, 1991.

*Primary Examiner*—Porfirio Nazario-Gonzalez
*Attorney, Agent, or Firm*—Mueting, Raasch & Gebhardt, P.A.

[57] ABSTRACT

A method of forming a film on a substrate using, Group III metal complexes, including Group IIIA metals and Group IIIB metals, which include the lanthanides. The complexes and methods are particularly suitable for the preparation of semiconductor structures using chemical vapor deposition techniques and systems.

24 Claims, 2 Drawing Sheets

METHODS, COMPLEXES, AND SYSTEMS FOR FORMING METAL-CONTAINING FILMS

This is a division of application Ser. No. 08/915,888, filed Aug. 21, 1997, now U.S. Pat. No. 5,874,131, which is incorporated herein by reference.

U.S. patent application Ser. No. 08/915,888 is a continuation-in-part of U.S. patent application Ser. No. 08/725,033 filed on Oct. 2, 1996 now abandoned, entitled Methods, Complexes, and System for Forming Metal-Containing Films which is incorporated herein by reference.

FIELD OF THE INVENTION

This invention relates to methods and complexes for forming metal-containing films, such as metal or metal alloy films, particularly during the manufacture of semiconductor structures. The complexes include a Group III metal and are particularly suitable for use in a chemical vapor deposition system.

BACKGROUND OF THE INVENTION

Aluminum is one of the three primary materials used today in semiconductor structures, the other two being silicon and silicon dioxide. It is primarily used in thin films as an interconnect between the specific structures formed on semiconductor substrates or substrate assemblies. Aluminum has been an important material in the fabrication of semiconductor structures because of its high conductivity, low resistivity (2.7 $\mu\Omega$-cm), strong adhesion to silicon and silicon dioxide, and low stress. Its use is expanding into other metallization applications as well. For example, it is being examined to replace tungsten in contact holes or vias (i.e., very small openings located, for example, between surface conductive paths and or "wiring" and active devices on underlying layers), which are getting narrower and deeper, and harder to fill with metal.

Aluminum alloys are also used in semiconductor structures, including alloys of aluminum with copper, titanium, etc., and combinations thereof. The addition of small quantities (typically, about 0.1–4%) of other metals to aluminum improves its resistance to electromigration and reduces the propensity of aluminum thin-films to form hillocks (i.e., protrusions on the aluminum film surface). Such alloyed films also have increased resistivity over that of pure aluminum films.

In some applications, aluminum films are deposited using sputtering techniques; however, sputtered aluminum is not very effective at filling contact holes or vias because of shoulders or overhangs that form at the contact holes. These overhangs can lead to the formation of keyhole-shaped avoids within the holes. Various collimation techniques help reduce this problem, but typically not enough to enable complete filling of very small geometries (e.g., less than about 0.5 $\mu$m). Therefore, it is desirable to use chemical vapor deposition (CVD) to form aluminum and aluminum alloy films.

Dimethylaluminum hydride (DMAH) has emerged as one of the preferred materials for aluminum metallization by CVD. A serious problem with this material, however, is its pyrophoricity. This problem has been addressed to some degree by the addition of amines to the compound to act as stabilizing Lewis base donors to the aluminum center. However, such precursor compounds are still pyrophoric, albeit to a lesser extent, and an additional complicating factor is introduced into the vapor pressure behavior of the precursor as a result of dissociation of the amine. Thus, there is a continuing need for methods and precursors for the deposition of aluminum and aluminum alloy films, as well as other Group III metal or metal alloy films, on semiconductor structures, particularly using vapor deposition processes.

SUMMARY OF THE INVENTION

The present invention provides complexes and methods for forming metal-containing films, particularly Group III metal-containing films on substrates, such as semiconductor substrates or substrate assemblies during the manufacture of semiconductor structures. As used herein, Group III is meant to include both Group IIIA metals (Al, Ga, In) and Group IIIB metals (Sc, Y, and the lanthanide series). The lanthanide series of metals (e.g., cerium, praseodymium, neodymium, etc.) are often also referred to as rare earth elements.

The method involves forming a metal-containirng film using a Group III metal complex, preferably a Group III metal hydride complex. The metal-containing film can be used in various metallization layers, particularly in multi-level interconnects, in an integrated circuit structure.

The metal-containing film can be a single Group III metal, or a metal alloy containing a mixture of Group III metals or a Group III metal and one or more metals or metalloids from other groups in the Periodic Chart, such as copper, silicon, titanium, vanadium, niobium, molybdenum, tungsten, etc. Furthermore, for certain preferred embodiments, the metal-containing film can be a nitride, phosphide, arsenide, stibnide, or combination thereof. That is, the metal-containing film can be a Group III–V (e.g., GaAs) semiconductor layer.

Thus, in the context of the present invention, the term "Group III metal-containing film" or simply "metal-containing film" includes, for example, relatively pure films of aluminum, gallium, indium, scandium, yttrium, lanthanum, cerium, praseodymium, or neodymium. The term also includes alloys of aluminum, gallium, indium, scandium, yttrium, lanthanum, cerium, praseodymium, or neodymium, for example, with or without other metals or metalloids, as well as complexes of these metals and alloys with Group V elements (N, P, As, Sb) or mixtures thereof. The terms "single Group III metal film" or "Group III metal film" refer to films of aluminum, gallium, indium, scandium, yttrium, lanthanum, cerium, praseodymium, or neodymium, for example. The term "metal alloy film" refers to films of aluminum, gallium, indium, scandium, yttrium, lanthanum. cerium, praseodymium, and/or neodymium alloys with or without other metals or metalloids. That is, if there are no metals or metalloids from groups in the Periodic Chart other than Group III, the alloy films contain combinations of aluminum, gallium, and indium, for example.

One preferred method of the present invention involves forming a film on a substrate, such as a semiconductor substrate or substrate assembly during the manufacture of a semiconductor structure, by providing a substrate (preferably, a semiconductor substrate or substrate assembly), and providing, a precursor comprising one or more complexes of the formula:

(Formula I)

wherein: M is a Group III (IIIA or IIIB) metal; each $R^1$, $R^2$, $R^3$, and $R^4$ group is independently H or an organic group; L is H or an organic group; x = 1 to 4; and y = 0 to 4; and forming a metal-containing film from said precursor on a surface of the substrate (preferably, a semiconductor substrate or substrate assembly). Using such methods the complexes of Formula I are converted in some manner (e.g., decomposed) and deposited on a surface to form a metal-contaiining film. Thus, the film is not simply a film of the complex of Formula I, but may contain only the Group III metal, M, or metal alloys, for example.

As used herein, Formula I is an empirical formula. That is, it expresses in simplest form the relative number of atoms in a molecule. Thus, the compounds of Formula I can be monomers, dimers, trimers, etc. Typically, however, they are monomers and Formula I is the actual molecular formula. Such complexes are typically referred to as "diazadiene" or "diazabutadiene" complexes.

The complexes of Formula I are typically neutral complexes and may be liquids or solids at room temperature. If they are solids, they are preferably sufficiently soluble in an organic solvent to allow for vaporization by flash vaporization, bubbling, microdroplet formation, etc. However, these complexes can also be vaporized or sublimed from the solid state using known chemical vapor deposition techniques.

Another method of forming a metal-containing film on a substrate, such as a semiconductor substrate or substrate assembly during the manufacture of a semiconductor structure, involves providing a substrate (preferably, a semiconductor substrate or substrate assembly), and providing a precursor comprising one or more complexes of the formula:

$$[(R^1)NC(R^2)C(R^3)N(R^4)]_xML_y \quad \text{(Formula I)}$$

wherein: M is a Group III metal; each $R^1$, $R^2$, $R^3$, and $R^4$ group is independently H or a $(C_1-C_{30})$organic group; L is H or a $(C_1-C_{30})$organic group, with the proviso that if M is of Group IIIA, at least one L is H; x=1 to 4; and y=0 to 4; vaporizing the precursor to form vaporized precursor; and directing the vaporized precursor toward the substrate to form a metal-containing film on a surface of the substrate (preferably, a semiconductor substrate or substrate assembly).

Preferred embodiments of the methods of the present invention involve the use of one or more chemical vapor deposition techmiques, although this is not necessarily required. That is, for certain embodiments, sputtering, spin-on coating, etc., can be used.

The methods of the present invention are particularly well suited for forming films on a surface of a semiconductor substrate or substrate assembly, such as a silicon wafer, with or without layers or structures formed thereon, used in forming integrated circuits. It is to be understood that the methods of the present invention are not limited to deposition on silicon wafers; rather, other types of wafers (e.g., gallium arsenide wafer, etc.) can be used as well. Also. the methods of the present invention can be used in silicon-on-insulator technology. Furthermore, substrates other than semiconductor substrates or substrate assemblies, can be used in the methods of the present invention. These include, for example, fibers, wires, etc. If the substrate is a semiconductor substrate or substrate assembly, the films can be formed directly on the lowest semiconductor surface of the substrate, or they can be formed on any of a variety of the layers (i.e., surfaces) as in a patterned wafer, for example. Thus, the term "semiconductor substrate" refers to the base semiconductor layer, e.g., the lowest layer of silicon material in a wafer or a silicon layer deposited on another material such as silicon-on-sapphire. The term "semiconductor substrate assembly" refers to the semiconductor substrate having one or more layers or structures formed thereon.

One preferred embodiment of the present invention includes a method of fabricating an interconnnect for use in an integrated circuit. The method includes the steps of providing a semiconductor structure comprising a contact hole, and forming an aluminum alloy in the contact hole, wherein the aluminum alloy comprises at least one Group III metal other than aluminum, and wherein the non-aluminum Group III metal is provided utilizing a chemical vapor deposition technique with a precursor comprising one or more complexes of the formula:

$$[(R^1)NC(R^2)C(R^3)N(R^4)]_xM \quad \text{(II)},$$

wherein: M is a Group III metal other than aluminum, each $R^1$, $R^2$, $R^3$, and $R^4$ group is independently H or an organic group; and x=1 to 4. Preferably, the aluminum is also provided using a complex of Formula (II) wherein M is Al.

Another preferred embodiment of the present invention includes a method of fabricating a metal line in an integrated circuit. The method includes the steps of providing a semiconductor structure comprising an active area, and forming an aluminum alloy on the structure such that the aluminum alloy is electrically connected to the active area, wherein the aluminum alloy comprises at least one Group III metal in addition to aluminum, and wherein the non-aluminum Group III metal is provided utilizing a chemical vapor depostion technique with a precursor comprising one or more complexes of the formula:

$$[(R^1)NC(R^2)C(R^3)N(R^4)]_xM \quad \text{(II)},$$

wherein: M is a Group III metal other than aluminum, each $R^1$, $R^2$, $R^3$, and $R^4$ group is independently H or an organic group; and x=1 to 4. Preferably, the aluminum is also provided using a complex of Formula (II) wherein M is Al.

Also, the present invention provides a hydride complex of the following empirical formulas: $[(R^1)NC(R^2)C(R^3)N(R^4)]$ MH (Formula III); $[(R^1)NC(R^2)C(R^3)N(R^4)]MH_2$ (Formula IV); $[(R^1)NC(R^2)C(R^3)N(R^4)]MHR^5$ (Formula V); $[(R^1)NC(R^2)C(R^3)N(R^4)]_2MH$ (Formula VI); $[(R^1)NC(R^2)C(R^3)N(R^4)]_2MHR^5$ (Formula VII); $[(R^1)NC(R^2)C(R^3)N(R^4)]_3MH$ (Formula VIII) wherein: M is a Group III metal (preferably, a Group IIIA metal, such as, Al, Ga, or In); $R^1$, $R^2$, $R^3$, and $R^4$ are each independently H or an organic group (preferably $R^2$ and $R^3$ are each H and $R^1$ and $R^4$ are each an organic group); and $R^5$ is an organic group. These are typically referred to as hydride diazabutadiene complexes. These complexes can be used in the methods described above as components of the precursor.

The present invention also provides a complex of Formula (I) wherein M is a Group IIIB metal; $R^1$, $R^2$, $R^3$, and $R^4$ are each independently an organic group; L is an organic group (preferably, an alkyl moiety); x=1 to 4; and y=1 to 4.

A chemical vapor deposition system is also provided. The system includes a deposition chamber having a substrate positioned therein; a vessel containing a precursor comprising one or more complexes of Formula I wherein M is a Group III metal, each $R^1$, $R^2$, $R^3$, and $R^4$ group is independently H or an organic group, L is H or an organic group, x=1 to 4, and y=0 to 4; and a source of an inert carrier gas for transferring the precursor to the chemical vapor deposition chamber.

DETAILED DESCRIPTION

Figure 1:
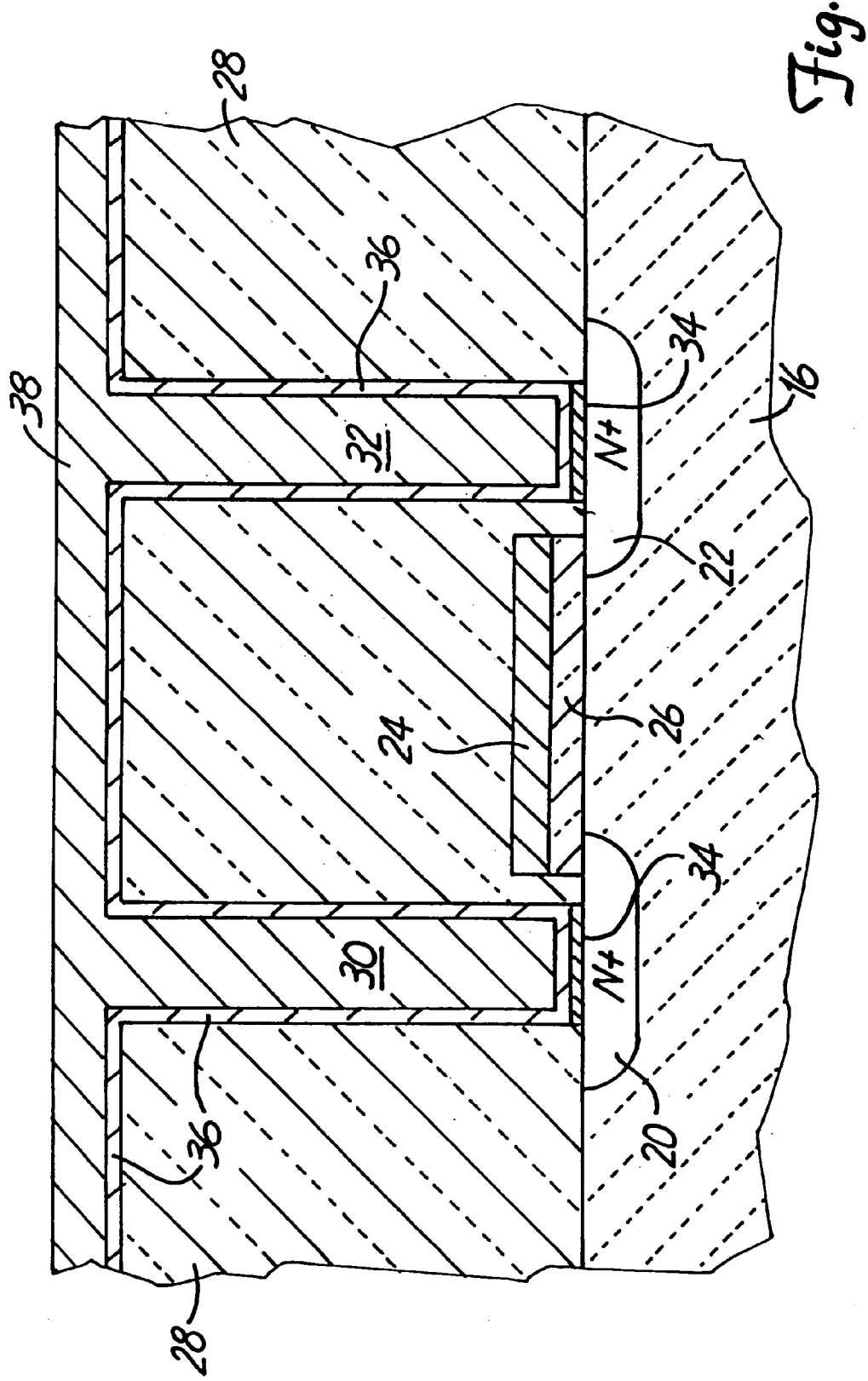
FIG. 1 is a cross-sectional schematic of a semiconductor contact or via having an aluminum film deposited in accordance with the method of the present invention.

The present invention provides a method of forming a Group III metal-containing film using one or more Group III metal complexes of Formula (I):

$$[(R^1)NC(R^2)C(R^3)N(R^4)]_xM \qquad (I),$$

wherein M is a Group III (IIIA or IIIB including lanthanides) metal; each $R^1$, $R^2$, $R^3$, and $R^4$ group is independently H or an organic group (preferably, a ($C_1$–$C_{30}$)organic group); L is H or an organic group (preferably, a ($C_1$–$C_{30}$)organic group); x=1 to 4; and y=0 to 4. In a preferred embodiment, complexes of Formula I are Group III metal hydride or alkyl complexes, and more preferably, Group IIIA metal hydride complexes or Group IIIB metal alkyl complexes. Preferably, such complexes are mononuclear (i.e., monomers in that they contain one metal per molecule). Thus, the complexes are preferably mononuclear diazadiene (i.e., diazabutadiene) complexes. Preferred embodiments display few intermolecular forces of attraction. However, it is also possible for one or more molecules of Formula I to combine to form dimers, trimers, etc., as is disclosed in Brown et al., *Inoriganic Chemistry*, 34, 6415–6416 (1995). Thus, the complexes of Formula I are expressed in their simplest form, i.e., Formula I is an empirical formula.

The complexes of Formula I preferably have vapor pressures sufficiently high such that they are volatile liquids at room temperature, although they can be solids. If they are solids, they are preferably soluble in organic solvents, such as aromatic and aliphatic hydrocarbons, nitrites, ethers, amines, etc., which allows for vaporization as a homogeneous mixture by direct liquid injection. They are also compatible with each other, so that mixtures of variable quantities of the complexes will not interact to significantly change their physical properties. Preferred embodiments are also generally nonpyrophoric.

Thus, many of the complexes described herein are suitable for use in chemical vapor deposition (CVD) techniques, such as flash vaporization techniques, bubbler techniques, and microdroplet techniques. However, these complexes can also be vaporized or sublimed from the solid state using other known CVD techniques. Preferred embodiments of the complexes described herein are particularly suitable for low temperature CVD, i.e., deposition techniques involving temperatures of about 50° C. to about 300° C.

One preferred method of the present invention involves vaporizing a precursor that includes one or more Group III metal complexes of Formula I. For certain embodiments, the precursor can also include one or more complexes containing metals or metalloids other than Group III metals. For example, the precursor can include Group V complexes (i.e., a compound containing N, P, As, or Sb). The precursor can also include copper and silicon complexes.

The precursor can be vaporized in the presence of an inert carrier gas to form a relatively pure metal or metal alloy film. The inert carrier gas is typically selected from the group consisting of nitrogen, helium, and argon. In the context of the present invention, an inert carrier gas is one that does not interfere with the formation of the metal-containing film.

Alternatively, the precursor can be vaporized in the presence of a reaction gas to form a film. The reaction gas can be selected from a wide variety of gases reactive with the complexes described herein, at least at a surface under the conditions of chemical vapor deposition. Examples of reaction gases include oxygen, nitrous oxide, ammonia, silane, water vapor, hydrogen sulfide, hydrogen selenide, hydrogen telluride. Various combinations of carrier gases and/or reaction gases can be used in the methods of the present invention to form metal-containing films.

Preferably, the Group III metal complexes of Formula I described herein are complexes having a coordination number of 3–8 with at least one diazabutadiene ligand, which is typically bidentate. The designation "hydride complex" refers to a Group III metal complex of Formula I containing at least one negatively charged hydride ligand in addition to the at least one diazabutadiene ligand, which can be neutral or negatively charged. Complexes such as these are advantageous because no other reaction compounds (e.g., reductants) are typically required to deposit the metal on a substrate and cleanly volatilize the ligands away without the incorporation of carbon and nitrogen impurities.

The Group III metal complex is of the followingy empirical formula:

$$[(R^1)NC(R^2)C(R^3)N(R^4)]_xML_y \qquad (\text{Formula I})$$

wherein: M is a Group III metal (i.e., a Group IIIA metal or Group IIIB metal including lanthanides, and preferably, Al, Ga, or In); each R (i.e., $R^1$, $R^2$, $R^3$, $R^4$) is independently H or an organic group; L is H or an organic group (preferably, with the proviso that if M is of Group IIIA, at least one L is H); x=1 to 4; y=0 to 4(preferably, y=1 to 4). The ligand $[(R^1)NC(R^2)C(R^3)N(R^4)]$ tipically bonds to the central metal through the nitrogen atoms. The ligands L can be organic groups that can be joined to form a ring or rings with the metal.

In another preferred embodiment, the metal complex is of the formula:

$$[(R^1)NC(R^2)C(R^3)N(R^4)]_xM \qquad (\text{Formula II})$$

wherein: M is a Group III metal; each $R^1$, $R^2$, $R^3$, and $R^4$ group is independently H or an organic group; and x=1 to 4.

A preferred class of complexes of Formula I include hydride complexes of the following empirical formulas: $[(R^1)NC(R^2)C(R^3)N(R^4)]_2MH$ (Formula III); $[(R^1)NC(R^2)C(R^3)N(R^4)]MH_2$ (Formula IV); $[(R^1)NC(R^2)C(R^3)N(R^4)]MHR^5$ (Formula V); $[(R^1)NC(R^2)C(R^3)N(R^4)]_2MH$ (Formula VI); $[(R^1)NC(R^2)C(R^3)N(R^4)]_2MHR^5$ (Formula VII); $[(R^1)NC(R^2)C(R^3)N(R^4)]_3MH$ (Formula VIII); wherein: M is a Group IIIA metal (preferably, a Group IIIA metal, such as, Al, Ga, or In); $R^1$, $R^2$, $R^3$, and $R^4$ are each independently H or an organic group (preferably $R^2$ and $R^3$ are each H and $R^1$ and $R^4$ are each an organic group); and $R^5$ is an organic group.

Another preferred class of complexes include complexes of the following empirical formula: $[(R^1)NC(R^2)C(R^3)N(R^4)]_xML_y$(Formula I), wherein M is a Group IIIB metal (preferably, Sc, Y, or La); $R^1$, $R^2$, $R^3$, and $R^4$ are each independently an organic group; L is an organic group; and x=1 to 4 and y=1 to 4. Preferably the organic groups are as defined herein.

As used herein, the term "organic group" means a hydrocarbon group that is classified as an aliphatic group, cyclic group, or combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example. The term "alk-yl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

In metal complexes such as those described herein, substitution is not only tolerated, but is often advisable. Thus, substitution is anticipated in the complexes of the present invention. As a means of simplifying the discussion and the recitation of certain terminology used throughout this application, the terms "group" and "moiety" are used to differentiate between chemical species that allow for substitution or that may be substituted and those that do not so allow or may not be so substituted. Thus, when the term "group" is used to describe a chemical substituent, the described chemical material includes the unsubstituted group and that group with nonperoxidic O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

For the R groups ($R^1$, $R^2$, $R^3$, $R^4$, and $R^5$) in the complexes of Formula I (including the complex of Formula II and the hydride complexes of Formulas III–VIII), H or ($C_1$–$C_{30}$)organic groups are preferred, H or ($C_1$–$C_{20}$)organic groups are more preferred, and H or ($C_1$–$C_8$)organic groups are most preferred. For certain embodiments, ($C_1$–$C_6$) organic groups are particularly preferred. Of the organic groups, nonaromatic groups (e.g., aliphatic groups and, alicyclic groups, which may or may not include unsaturation, and which may or may not include heteroatoms such as N, O, S, P, Si, etc.) are preferred. Of these, the aliphatic groups are more preferred, and alkyl moieties (particularly "lower" ($C_1$–$C_4$)alkyl moieties) are most preferred. Thus, for particularly preferred complexes of Formula I, each R group can be H or a ($C_1$–$C_4$)alkyl moiety.

The complexes of Formula I are typically neutral complexes and may be liquids or solids at room temperature. If they are solids, they are preferably sufficiently soluble in an organic solvent to allow for vaporization by flash vaporization, bubbling, microdroplet formnation, etc. However, these complexes can also be vaporized or sublimed from the solid state using known chemical vapor deposition techniques.

Various combinations of the complexes described herein can be used in precursors for chemical vapor deposition. Alternatively, certain complexes described herein can be used in other deposition techniques, such as sputtering, spin-on-coating, and the like. Typically, those complexes containing R groups with a low number of carbon atoms (e.g., 1–4 carbon atoms per R group) are suitable for use with CVD techniques. Those complexes containing R groups with a higher number of carbon atoms (e.g., 5–12 carbon atoms per R group) are generally suitable for spin-on or dip coating. Preferably, however, CVD techniques are desired because they are more suitable for deposition on semiconductor substrates or substrate assemblies, particularly in contact openings which are extremely small and require conformally filled layers of metal.

For the preparation of alloy films, two or more complexes of Formula I can be combined in a precursor mixture (e.g., AlH($^i$Pr—NCHCHN—$^i$Pr) and GaH($^i$PrNCHCHN—$^i$Pr) for an Al—Ga alloy). Alternatively, at least one complex of Formula I can be combined with another complex in a precursor mixture (e.g., AlH($^i$Pr—NCHCHN—$^i$Pr) and CuPMe$_3$(hfac) for an Al—Cu alloy). For preparation of an aluminum film alloyed with a Group IIIB metal, a suitable metal alloy element (e.g. Sc($^i$Pr—NCHCHN—$^i$Pr)$_2$ and Y($^t$Bu—NCHCHN—$^t$Bu)$_3$) can be combined in a precursor mixture with an aluminum complex (e.g., dimethylaluminum hydride (DMAH)) to form the aluminum alloy film. For preparation of films containing Group III–V (e.g., GaAs) semiconductor materials, the precursors described herein contain one or more complexes of Formula I and an appropriate source of the Group V element. Such sources of Group V elements include compounds such as $NH_3$, $PH_3$, $AsH_3$, $Me_3As$, $Me_3Sb$, $Me_3P$, $EtAsH_2$, $Me_2{}^tBuSb$, etc.

The complexes of the present invention can be prepared by a variety of methods known to one of skill in the art. For example, AlH($^i$Pr—NCHCHN—$^i$Pr) can be prepared by reaction of AlCl$_3$ with Li$_2$($^i$Pr—NCHCHN—$^i$Pr) followed by reduction with LiAlH$_4$. Y($^t$Bu—NCHCHN—$^t$Bu)$_3$ can be prepared by the condensation reaction of yttrium metal vapor with the $^t$Bu-diazadiene (i.e., $^t$Bu—N=CHCH=N—$^t$Bu) ligand in heptane. Sc($^i$Pr—NCHCHN—$^i$Pr)$_2$ can be prepared by the condensation reaction of scandium vapor with the $^i$Pr-diazadiene ligand. The lanthanum complex, CpLa($^i$Pr—NCHCHN—$^i$Pr) can be prepared by reaction of CpLaCl$_2$(THF)$_n$(wherein Cp=cyclopentadienyl) and Li$_2$ ($^i$Pr—NCHCHN—$^i$Pr).

As stated above, the use of the complexes of Formula I and methods of forming metal-containing films of the present invention are beneficial for a wide variety of thin film applications in semiconductor structures, particularly various metallization layers. Such applications include multilevel interconnects in an integrated circuit structure. For example, the methods and complexes of the present invention can be used to fabricate an interconnect by forming an aluminum alloy in a contact hole, or to fabricate a metal line by forming an aluminum alloy electrically connected to an active area in a semiconductor structure. Typically, thin films of Group III metals, such as aluminum, and alloys thereof are deposited as polycrystalline materials, usually in the 0.5–1.5 μm thickness range.

A specific example of where a film formed from the complexes of the present invention would be useful is the structure shown in FIG. 1. The structure may be in the form of an n-channel MOSFET (n-chanmel metal-oxide semiconductor field-effect transistor), which may be used in a DRAM (dynamic random access memory) device. As shown, substrate 16 is a p-type silicon having two n-type silicon islands 20 and 22, representing the transistor source and drain. Such a construction is well known. The gate for the transistor is formed by a metal/polysilicon layer 24 deposited over a silicon dioxide layer 26. A relatively thick layer of an insulating silicon dioxide 28 overlies the active areas on substrate 16.

To connect the MOSFET with electrically conductive paths (i.e., metal lines) on the surface of the device, contacts 30 and 32 hive been etched through oxide layer 28 down to the surface of substrate 16. A metal or metal silicide layer 34, such as titanium silicide, is deposited and formed at the base of contact holes 30 and 32. A thin, conformal barrier layer of a refractory metal nitride 36 (e.g., titanium nitride, titanium aluminum nitride, titanium nitride silicide) is deposited over the walls of the contact holes 30 and 32. Because of the presence of the conductive barrier layer 36, the electrical contact path is excellent and the aluminum alloy metal 38 which is deposited over the refractory metal nitride barrier layer is prevented from attacking the substrate surfaces. The aluminum alloy metal 38 comprises at least one metal selected from the Group III mcetals. The aluminum alloy metal 38 is also used for metal lines overlying active areas of the semiconductor structure. For example, metal lines are utilized to electrically connect active areas via contacts 30, 32, formed as described above.

The method of the present invention can be use: to deposit a metal-containing film, preferably a metal or metal alloy film, on a variety of substrates, such as a semiconductor wafer (e.g., silicon wafer, gallium arsenide wafer, etc.), glass plate, etc., and on a variety of surfaces of the substrates, whether it be directly on the substrate itself or on a layer of material deposited on the substrate as in a semiconductor substrate assembly. The film is typically deposited upon thermal decomposition of a Group III metal complex of Formula I that is preferably either liquid at the temperature of deposition or soluble in a suitable solvent that is not detrimental to the substrate, other layers thereon, etc. Preferably, however, solvents are not used; rather, the Group III metal complexes of Formula I are liquid and used neat. The method of the present invention preferably utilizes vapor deposition techniques, such as flash vaporization, bubbling, etc.

Conventional bubbler technology can be used to form films from the complexes of Formula I described above. In conventional bubbler technology, a carrier gas, typically nitrogen, is bubbled through the precursor (which is either a liquid or a solid dissolved in a liquid solvent) to sweep some of the precursor molecules into the processing chamber.

Alternatives to conventional bubbler technology include an approach wherein the precursor is heated and vapors are drawn off and controlled by a vapor mass flow controller. Further, another way is to pump the gas through the precursor using either a very precise metering pump or a liquid mass flow controller up to the point where it enters the reaction chamber. At that point, it can either be flash vaporized or injected directly into a mixing chamber and showerhead where it is vaporized. As described in the article entitled, "Metalorganic Chemical Vapor Deposition By Pulsed Liquid Injection Using An Ultrasonic Nozzle: Titanium Dioxide on Sapphire from Titanium (IV) Isopropoxide," by Versteeg, et al., *Journal of the American Ceramic Society*, 78, 2763–2768 (1995) a metalorganic CVD process utilizes pulsed on/off liquid injection in conjunction with atomization by an ultrasonic, piezoelectrically driven nozzle to deliver such metalorganic precursors. The pulse injection is said to allow control of film deposition rates, as fine as monolayers per pulse. The ultrasonic nozzle provides a mist of droplets into the processing chamber of a reactor for reproducible vaporization of the liquid precursor. Such a delivery system performs the vaporization in the processing chamber.

The complexes of Formula I are particularly wvell suited for use with vapor deposition systems, as described in copending application U.S. Ser. No. 08/720,710 entitled "Method and Apparatus for Vaporizing Liquid Precursors and System for Using Same," filed Oct. 2, 1996. Generally, using the method described therein, the vaporization of a liquid precursor or precursor dissolved in a liquid medium is carried out in two stages. First, the precursor is atomized or nebulized generating high surface area microdroplets or mist. In the second stage, the constituents of the microdroplets or mist are vaporized by intimate mixture of the heated carrier gas. This two stage vaporization approach provides a reproducible delivery for precursors (either liquid or dissolved in a liquid medium) and provides reasonable growth rates, particularly in device applications faith small dimensions.

Figure 2:
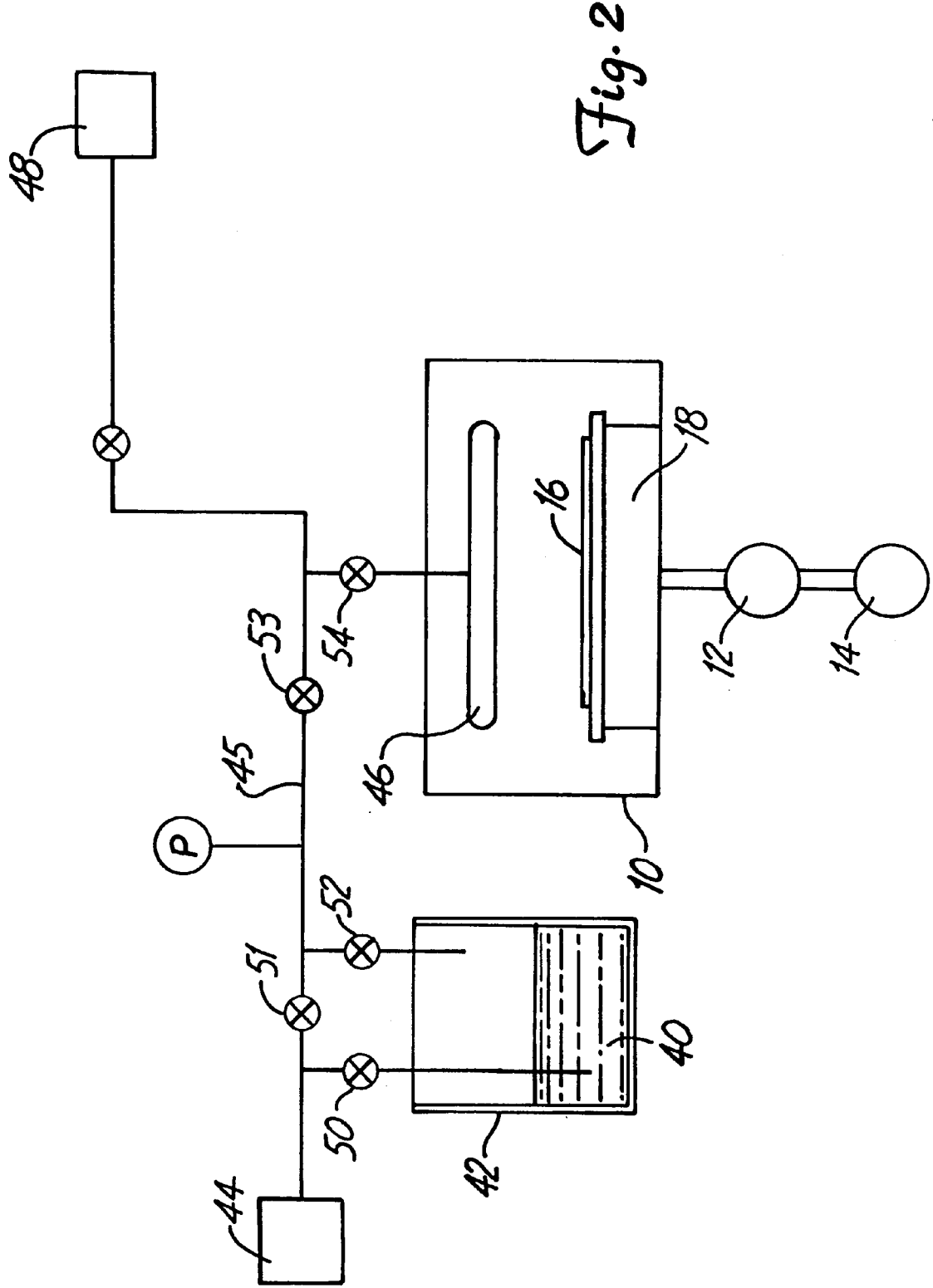
FIG. 2 is a schematic of a chemical vapor deposition system suitable for use in the method of the present invention.

A typical chemical vapor deposition (CVD) system that can be used to perform the process of the present invention is shown in FIG. 2. The system includes an enclosed CVD chamber 10, which may be a cold wall-type CVD reactor. As is conventional, the CVD process may be carried out at pressures of from atmospheric pressure down to about $10^{-3}$ torr, and preferably from about 1.0–0.1 torr. A vacuum may be created in chamber 10 using turbo pump 12 and backing pump 14.

One or more substrate structures 16 (e.g., semiconductor substrates or substrate assemblies) are positioned in chamber 10. A constant nominal temperature is established for the substrate, preferably, at a temperature of about 0° C. to about 600° C., and more preferably, at a temperature of about 50° C. to about 300° C. Substrate 16 may be heated, for example, by an electrical resistance heater 18 on which substrate 16 is mounted. Other known methods of heating substrate 16 may also be utilized.

In this process, the precursor 40, which contains one or more complexes of Formula I, is stored in liquid form in vessel 42. A source 44 of a suitable inert gas is pumped into vessel 42 and bubbled through the liquid, picking up the precursor and carrying it into chamber 10 through line 45 and gas distributor 46. Additional inert carrier gas may be supplied from source 48 as needed to provide the desired concentration of precursor and regulate the uniformity of the deposition across the surface of substrate 16. As shown, a series of valves 50–54 are opened and closed as required.

Generally, the precursor is pumped into the CVD chamber 10 at a flow rate of about 1–1000 sccm (standard cubic centimeter per minute). The semiconductor substrate is exposed to the precursor at a pressure of about 0.001–100 torr for a time of about 0.01–100 minutes. In chamber 10, the precursor will form an adsorbed layer on the surface of the refractory metal nitride 36( (FIG. 1). As the deposition rate is temperature dependent, increasing the temperature of the substrate will increase the rate of deposition. Typical deposition rates are about 1000–10,000 Å/minute. The carrier gas containing the precursor is terminated by closing valve 53.

Various combinations of carrier gases and/or reaction gases can be used in certain methods of the present invention. They can be introduced into the chemical vapor deposition chamber in a variety of manners, such as directly into the vaporization chamber, in combination with the precursor, in combination with (or in place of) the carrier gas.

The following examples are offered to further illustrate the various specific and preferred embodiments and techniques. It should be understood, however, that many variations and modifications may be made while remaining within the scope of the present invention.

EXAMPLES

Example 1
Preparation of Al[($^t$Bu)NCHCHN($^t$Bu)]$_2$

This compound is prepared as described in Clokce et al., *J. Chem. Soc., Chem. Commun.*, 1394 (1990).

Example 2
Preparation of Ga(C$_2$H$_5$)[($^t$Bu)NCHCHN($^t$Bu)]

In an inert atmosphere in a glove box, Ga(C$_2$H$_5$)Cl$_2$(1.70 g, 10 mmol) is added to a dry flask and dissolved in 20 mL of toluene. The solution is cooled to −78° C. To it is added 10 mmol of Li$_2$[($^t$Bu)NCHCHN($^t$Bu)], which is prepared by addition of Li foil (0.14 g, 20 mmol) to bis-tert-butyldiazabutadiene (1.68 g, 10 mmol) in 30 mL of toluene. The mixture is allowed to slowly warm to room temperature, and the solvent is then removed in vacuo. The product is then sublimed from this crude mixture.

Example 3
Preparation of AlH[($^t$Bu)NCHCHN($^t$Bu)]

In an inert atmosphere in a glove box, AlCl$_3$ (2.66 g, 20 mmol) is added to a dry flask and suspended in 40 mL of toluene. The mixture is cooled to −78° C. To it is added 20 mmol of Li$_2$[($^t$Bu)NCHCHN($^t$Bu)], which is prepared by addition of Li foil (0.28 g, 40 mmol) to bis-tert-butyldiazabutadiene (3.36 g, 20 mmol) in 50 mL of toluene. The mixture is allowed to slowly warm to room temperature. The solution is then added to a suspension of LiAlH$_4$(0.76 g, 20 mmol) in cooled toluene (−78° C.). The solvent is removed in vaczio and the product is sublimed from the crude residue.

Example 4
Preparation of Y[($^t$Bu)NCHCHN($^t$Bu)]$_3$

This compound is prepared as described in Cloke et al., *J. Chem. Soc., Chem. Commun.*, 1344–45 (1986).

Example 5
Preparation of Nd[($^t$Bu)NCHCHN($^t$Bu)]$_3$

This compound is prepared as described in Cloke et al., *J. Chem. Soc., Chem. Commun.*, 1344–45 (1986).

Example 6
Preparation of Sm[($^t$Bu)NCHCHN($^t$Bu)]$_3$

This compound is prepared as described in Cloke et al., *J. Chem. Soc., Chem. Commun.*, 1344–45 (1986).

Example 7
Preparation of Yb[($^t$Bu)NCHCHN($^t$Bu)]$_3$

This compound is prepared as described in Cloke et al., *J. Chem. Soc., Chem. Commun.*, 1344–45 (1986).

Example 8
Preparation of Aluminum Thin Films

A patterned semiconductor wafer is loaded into a CVD chamber, and the wafer heated to approximately 250° C. The precursor, Al[($^t$Bu)NCHCHN($^t$Bu)]$_2$, is loaded into a conventional stainless steel bubbler inside a glove box, and the bubbler transferred to the CVD system. A helium carrier gas flow of 50 standard cubic centimeters per minute (sccm) is established through the bubbler, and a chamber pressure of 0.25 torr is established. The deposition is carried out until a desired thickness of aluminum is obtained on the wafer.

Example 9
Preparation of Yttrium Thin Films

A patterned semiconductor wafer is loaded into a CVD chamber, and the wafer heated to approximately 250° C. The precursor, Y[($^t$Bu)NCHCHN($^t$Bu)]$_3$, is loaded into a conventional stainless steel bubbler inside a glove box, and the bubbler is transferred to the CVD system. A helium carrier gas flow of 50 standard cubic centimeters per minute (sccm) is established through the bubbler, and a chamber pressure of 0.25 torr is established. The deposition is carried out until a desired thickness of yttrium is obtained on the wafer.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims. The complete disclosures of all patents, patent documents, and publications listed herein are incorporated by reference, as if each were individually incorporated by reference.

What is claimed is:

1. A hydride complex of the formula:

$$[(R^1)NC(R^2)C(R^3)N(R^4)]MH \qquad \text{(Formula III)}$$

wherein:

M is a Group IIIB metal; and $R^1, R^2, R^3$, and $R^4$ are each independently H or an organic group.

2. A hydride complex of the formula:

$$[(R^1)NC(R^2)C(R^3)N(R^4)]MH_2 \qquad \text{(Formula IV)}$$

wherein:

M is a Group IIIA metal; and $R^1, R^2, R^3$, and $R^4$ are each independently H or an organic group.

3. A hydride complex of the formula:

$$[(R^1)NC(R^2)C(R^3)N(R^4)]MHR^5 \qquad \text{(Formula V)};$$

wherein:

M is a Group IIIA metal;

$R^1, R^2, R^3$, and $R^4$ are each independently H or an organic group; and $R^5$ is an organic group.

4. A hydride complex of the formula:

$$[(R^1)NC(R^2)C(R^3)N(R^4)]_2MH \qquad \text{(Formula VI)}$$

wherein:

M is a Group IIIA metal; and $R^1, R^2, R^3$, and $R^4$ are each independently H or an organic group.

5. A hydride complex of the formula:

$$[(R^1)NC(R^2)C(R^3)N(R^4)]_2MHR^5 \qquad \text{(Formula VII)}$$

wherein:

M is a Group IIIA metal;

$R^1, R^2, R^3$, and $R^4$ are each independently H or an organic group; and $R^5$ is an organic group.

6. A hydride complex of the formula:

$$[(R^1)NC(R^2)C(R^3)N(R^4)]_3MH \qquad \text{(Formula VIII)}$$

wherein:

M is a Group IIIA metal; and $R^1, R^2, R^3$, and $R^4$ are each independently H or an organic group.

7. A complex of the formula:

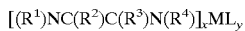 (Formula I)

wherein:
M is a Group IIIB metal;
each $R^1$, $R^2$, $R^3$, and $R^4$ group is independently an organic group;
L is an organic group;
x=1 to 4; and
y=1 to 4.

8. The complex of claim 7 wherein M is Sc, Y, or La.

9. The complex of claim 7 wherein L is an alkyl moiety.

10. A hydride complex of the formula:

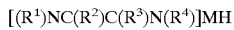 (Formula III)

wherein:
M is Al; and
$R^1$, $R^2$, $R^3$, and $R^4$ are each independently H or an organic group.

11. The hydride complex of claim 1 wherein each $R^1$, $R^2$, $R^3$, and $R^4$ group is independently H or a ($C_1$–$C_{30}$) organic group.

12. The hydride complex of claim 1 wherein each $R^1$, $R^2$, $R^3$, and $R^4$ group is independently H or a ($C_1$–$C_4$) alkyl moiety.

13. The hydride complex of claim 2 wherein each $R^1$, $R^2$, $R^3$, and $R^4$ group is independently H or a ($C_1$–$C_{30}$) organic group.

14. The hydride complex of claim 2 wherein each $R^1$, $R^2$, $R^3$, and $R^4$ group is independently H or a ($C_1$–$C_4$) alkyl moiety.

15. The hydride complex of claim 3 wherein each $R^1$, $R^2$, $R^3$, and $R^4$ group is independently H or a ($C_1$–$C_{30}$) organic group and $R^5$ is a ($C_1$–$C_{30}$) organic group.

16. The hydride complex of claim 3 wherein each $R^1$, $R^2$, $R^3$, and $R^4$ group is independently H or a ($C_1$–$C_4$) alkyl moiety and $R^5$ is a ($C_1$–$C_4$) alkyl moiety.

17. The hydride complex of claim 4 wherein each $R^1$, $R^2$, $R^3$, and $R^4$ group is independently H or a ($C_1$–$C_{30}$) organic group.

18. The hydride complex of claim 4 wherein each $R^1$, $R^2$, $R^3$, and $R^4$ group is independently H or a ($C_1$–$C_4$) alkyl moiety.

19. The hydride complex of claim 5 wherein each $R^1$, $R^2$, $R^3$, and $R^4$ group is independently H or a ($C_1$–$C_{30}$) organic group and $R^5$ is a ($C_1$–$C_{30}$) organic group.

20. The hydride complex of claim 5 wherein each $R^1$, $R^2$, $R^3$, and $R^4$ group is independently H or a ($C_1$–$C_4$) alkyl moiety and $R^5$ is a ($C_1$–$C_4$) alkyl moiety.

21. The hydride complex of claim 6 wherein each $R^1$, $R^2$, $R^3$, and $R^4$ group is independently H or a ($C_1$–$C_{30}$) organic group.

22. The hydride complex of claim 6 wherein each $R^1$, $R^2$, $R^3$, and $R^4$ group is independently H or a ($C_1$–$C_4$) alkyl moiety.

23. The hydride complex of claim 7 wherein each $R^1$, $R^2$, $R^3$, and $R^4$ group is independently H or a ($C_1$–$C_{30}$) organic group.

24. The hydride complex of claim 7 wherein each $R^1$, $R^2$, $R^3$, and $R^4$ group is independently H or a ($C_1$–$C_4$) alkyl moiety.

* * * * *

UNITED STATES PATENT AND TRADEMARK OFFICE
CERTIFICATE OF CORRECTION

PATENT NO.: 6,020,511
DATED: February 1, 2000
INVENTOR(S): Vaartstra et al.

It is certified that error appears in the above-identified patent and that said Letters Patent is hereby corrected as shown below:

Face page, item "[56] References Cited", "Cloke et al., Paramagnetic Aluminum" reference, delete "$CH_2\{_2$", and insert --$CH_2\}_2$--;

Face page, item "[56] References Cited", "Gluz et al.," reference, after "Quantum", insert -- - --;

Face page, item "[57] ABSTRACT", line 1, after "using", delete ",";

Column 1, line 53, delete "avoids", and insert --voids--;

Column 2, line 18, delete "containirng", and insert --containing--;

Column 3, line 3, delete "contaiining", and insert --containing--;

Column 5, line 30, delete "nitrites", and insert --nitriles--;

Column 6, line 15, delete "followingy", and insert --following--;

Column 6, line 25, delete "tipically", and insert --typically--;

Column 7, line 49, delete "and,", and insert --and--;

Column 7, line 61, delete "formnation", and insert --formation--;

Column 8, line 15, after "GaH($^i$Pr", insert -- - --;

Column 9, line 17, delete "mcetals", and insert --metals--;

UNITED STATES PATENT AND TRADEMARK OFFICE
CERTIFICATE OF CORRECTION

PATENT NO.: 6,020,511
DATED: February 1, 2000
INVENTOR(S): Vaartstra et al.

It is certified that error appears in the above-identified patent and that said Letters Patent is hereby corrected as shown below:

Column 9, line 22, delete "use:", and insert --used--;

Column 10, line 1, delete "wvell", and insert --well--;

Column 10, line 51, delete "36(", and insert --36--;

Column 11, line 5, delete "Clokce", and insert --Cloke--;

Column 11, line 20, delete "AIH", and insert --AlH--; and

Column 11, line 30, delete "vaczio", and insert --vacuo--.

Signed and Sealed this

Twenty-ninth Day of May, 2001

*Attest:*

NICHOLAS P. GODICI

*Attesting Officer*     *Acting Director of the United States Patent and Trademark Office*